(12) United States Patent
Smeeding et al.

(10) Patent No.: US 9,218,608 B2
(45) Date of Patent: Dec. 22, 2015

(54) PRESCRIPTION DRUG DISCOUNT AND THERAPY DELIVERY SYSTEMS AND METHODS

(71) Applicant: Digital Health Dialog, LLC, South Lake, TX (US)

(72) Inventors: James E. Smeeding, Dallas, TX (US); Kenneth Burkett, South Lake, TX (US)

(73) Assignee: Digital Health Dialog, LLC

( * ) Notice: Subject to any disclaimer, the term of this patent is extended or adjusted under 35 U.S.C. 154(b) by 0 days.

(21) Appl. No.: 13/837,517

(22) Filed: Mar. 15, 2013

(65) Prior Publication Data

US 2013/0275196 A1 Oct. 17, 2013

Related U.S. Application Data

(63) Continuation of application No. 12/463,446, filed on May 11, 2009, now Pat. No. 8,452,608.

(51) Int. Cl.
| | |
|---|---|
| *G06Q 10/00* | (2012.01) |
| *G06Q 30/02* | (2012.01) |
| *G06F 19/00* | (2011.01) |
| *G06Q 50/22* | (2012.01) |
| *G06Q 50/24* | (2012.01) |

(52) U.S. Cl.
CPC ........ *G06Q 30/0225* (2013.01); *G06F 19/3456* (2013.01); *G06Q 30/02* (2013.01); *G06Q 30/0234* (2013.01); *G06Q 50/22* (2013.01); *G06Q 50/24* (2013.01)

(58) Field of Classification Search
CPC ....... G06Q 30/06; G06Q 30/02; G06Q 50/22; G06Q 30/0207
USPC ...................... 705/2, 3, 14.64, 14.1
See application file for complete search history.

(56) References Cited

U.S. PATENT DOCUMENTS

2006/0229915 A1* 10/2006 Kosinski et al. .................. 705/2
2009/0048712 A1* 2/2009 Rosenblum ................... 700/242

\* cited by examiner

*Primary Examiner* — Michelle L Le
(74) *Attorney, Agent, or Firm* — The Law Firm of H. Dale Langley, Jr., P.C.

(57) ABSTRACT

A method of delivering a discount on a purchasable item via a cellular message includes capturing a token of the item by a cellular device. The cellular device processes the token and sends a message artifact as a cellular message, such as SMS message. A discount service computer receives and parses the message artifact, and reconstructs the token. The token is matched to a record of an eligibility database, if any exist, or else a corresponding record for the token is generated. A discount database is accessed for a discount coupon relevant to the record and the purchasable item identity. The discount coupon is sent to the cellular device as a text message. A benefit processor may adjudicate an insured coverage, if applicable. The item is discounted at point of purchase, accounting for any insurance coverage, and the applicable record of the discount database is updated.

27 Claims, 8 Drawing Sheets

PRESCRIPTION DRUG DISCOUNT AND THERAPY DELIVERY SYSTEMS AND METHODS

CROSS-REFERENCE TO RELATED APPLICATIONS

The present application is a continuation and has benefit of priority of U.S. patent application Ser. No. 12/463,446, titled "Wireless Cellular Systems and Methods for Prescription Drug Discounts and Therapy Delivery", filed May 11, 2009, which application is co-pending and has at least one same inventor of the present application and is herein incorporated by this reference.

TECHNICAL FIELD

The present disclosure relates generally to communication networks and wireless devices for delivery of prescription drugs and drug therapy, and, more particularly, relates to wireless and networked communication devices, including, but not limited to, cellular telephones, for delivery of prescription drugs, medication therapy management, patient discounts, and advertising.

BACKGROUND

Conventionally, a medical patient obtains a written script for a prescription drug from a physician to address the patient's malady. The patient carries the written script to a pharmacy. The pharmacy fills the prescription. The patient makes payment and picks-up the prescription drug at the pharmacy. The price paid by the patient is the pharmacy's charge for the drug less any covered benefit under the patient's insurance. The pharmacy collects the covered benefit amount from the insurer. Streamline of this conventional prescription drug delivery process would benefit patients, and also pharmacies and other health providers.

In this conventional prescription drug delivery scheme, the pharmacist typically instructs the patient in proper use of the drug at point of pick-up by the patient at the pharmacy. During the patient's visit to the physician's office, the physician may also provide the patient with drug use and protocol instruction. These instructions (whether from pharmacist and/or physician) may be verbal, written, or combination. Typical instructions may include proper drug use procedures, regimen schedule, importance of regimen compliance, and others. After the patient's contact with the pharmacist and physician, the patient must retain and recollect the instructions, in whatever form received. Often, the patient's only next opportunity to confirm the instructions is a subsequent face-to-face contact with the physician or pharmacist, such as through a later physician office or pharmacy visit for a medication check-up or prescription refill.

Physicians, pharmacies, insurers, and other pharmaceutical and health providers are interested in targeting helpful and applicable information to prescription drug patients. Time and access constraints of these providers limit opportunity for disseminating such information to the patient. Benefit insurers, for example, wish to encourage patient compliance to drug therapy regimen and to promote healthy practices. Physicians desire greater access to patients for increased awareness of patient efforts and concerns during drug therapy, such as would assist improving and varying drug treatment as appropriate. Pharmacies similarly wish to assist patients by providing helpful targeted information, addressing patient questions, and promoting health and marketing initiatives.

Patients desire access to uniquely targeted information to gain knowledge about specific prescription drugs and options and to assist the patient's medication therapy, proper drug usage, and health practices. Patient access to credible sources of information has conventionally been limited because periods of the patient's direct contact with physicians, pharmacists and other health providers are often time constrained. Patients, moreover, may not have ability to assess credibility of information that may be available from third party sources. Additionally, even where the patient has been provided credible relevant information (such as by physician, pharmacy or other reliable source), patients may misplace such information or tend to disregard the information if not readily and easily accessible. Targeted drug and health information, uniquely relevant to the patient and applicable prescription, would be beneficial if readily accessible to patients.

Cellular telephones and other wireless devices are a prevalent mode of communication for many consumers. These consumers include prescription drug patients and patient caregivers. Cellular devices can provide features for voice calls, messaging, calendar, scheduling, Internet access, and other operations. Cellular telephones, for example, in addition to voice call capabilities, often have short message service (SMS), multimedia message service (MMS), enhanced message service (EMS), wireless access protocol service (WAP), and/or other messaging features for sending and receiving mobile text and multimedia communications.

It would, therefore, be desirable to provide new and improved systems and methods for communicating targeted uniquely relevant information and streamlining prescription drug delivery to prescription drug patients. It would also be desirable to limit burden to patients, as well as to physicians, pharmacies, insurers and other providers, of prescription drug delivery, drug cost and drug therapy management.

SUMMARY

An embodiment of the invention is a method of delivering a prescription drug discount via a cellular message on a cellular carrier network. The method includes capturing a prescription token in a memory of a cellular communication device. The prescription token includes at least one instructor, including a prescription drug identity, a prescription drug patient identity, a cell phone number related to the prescription drug patient identity, and at least one destination locator for a server computer communicatively connected to the cellular carrier network. The method also includes processing a message artifact of the prescription token by the cellular communication device for a destination address of a server computer communicatively accessible by the cellular carrier network, transmitting the message artifact by the cellular communication device over the cellular carrier network, receiving the message artifact by the server computer at the destination address, parsing the message artifact by the server computer, and generating the prescription token by the server computer. The method further includes looking-up the prescription token, or portions, in an eligibility database connected to the server computer to find an eligibility record related to the prescription token, retrieving the eligibility record, looking-up the eligibility record, or portions, in a discount database to obtain a discount artifact related to the prescription drug identity for the prescription token, retrieving the discount artifact, processing the discount artifact by the server computer to generate a discount coupon, and sending the discount coupon to the cellular communication device on the cellular carrier network. The method also includes receiving the discount coupon by the cellular communication device from the cellular carrier network and presenting the discount coupon, together with a drug prescription per the prescription drug identity, to a pharmacy gateway. Additionally, the method includes communicating the drug prescription, together with the prescription drug patient identity, to a benefit processor, determining a coverage benefit by the benefit processor, communicating the coverage benefit to the pharmacy gateway, and communicating an eligibility update notification to the server computer by the benefit processor. Furthermore, the method includes receiving the eligibility update notification by the server computer, updating the eligibility record of the eligibility database in response to the eligibility update notification, processing the eligibility update notification to derive a prescription refill date related to the eligibility record, and storing the prescription refill date in the eligibility record.

In further embodiments, the method includes, if the step of looking-up the prescription token fails because the eligibility record is not in the eligibility database, prior to the step of retrieving the eligibility record, generating an eligibility record by the eligibility database based on the prescription token.

In yet further embodiments, the updating of the method includes processing the eligibility update notification by the benefit processor to revise the eligibility record.

In other further embodiments, the coverage benefit is selected from the group consisting of: an insured coverage and a non-insured coverage; and the method includes, if an insured coverage is the coverage benefit, determining by the pharmacy gateway a first discount per the coverage benefit and the discount coupon, for the drug prescription, and, if a non-insured coverage is the coverage benefit, determining by the pharmacy gateway a second discount per solely the discount coupon, for the drug prescription.

In additional embodiments, the eligibility database comprises a plurality of eligibility records, and each of the eligibility records includes the prescription drug identity, the drug patient identity, the prescription refill date, and the cell number relationally linked to the drug patient identity, and the method includes filtering the plurality of the eligibility records at a date in time, based on the date in time and relation to the prescription refill date of the eligibility records, retrieving a subset of the plurality for the prescription drug identity, the prescription refill date relative to the date in time, and the cell number relationally linked to the respective drug patient identity and the prescription drug identity, looking-up the prescription drug identity of the subset in the discount database to obtain a respective discount coupon for each prescription drug identity of the subset, retrieving the respective discount coupon, sending the respective discount coupon to the cell number relationally linked to the applicable drug patient identity and the drug identity of the relevant eligibility record(s), and repeating for the entire subset and all prescription drug identities of the subset.

Another embodiment of the invention is a system for delivering a prescription drug discount via a cellular message of a carrier network. The system includes a prescription script and a cell phone relationally connected to the prescription script. The cell phone includes a processor, a radio connected to the processor, a phone number communicatively accessible on the carrier network, a prescription token of the cell phone communicated by the radio of the cell phone on the carrier network, and an output interface of the cell phone connected to the processor. A server computer of the system is communicatively connected to the cell phone via the carrier network, to receive the prescription token. The system also includes an eligibility database and a discount database of the server computer, and the server computer controls the eligibility database and the discount database in response to receiving the prescription token. The system further includes a discount coupon of the discount database, communicated by the server computer to the cell phone at the phone number via the carrier network, in response to receiving the prescription token. A pharmacy gateway of the system is communicatively connected to the cell phone to receive the discount coupon from the cell phone and the prescription script. A benefit processor of the system is communicatively connected to the pharmacy gateway and the server computer. The benefit processor includes a database, a benefit artifact of the database relationally associated to the discount coupon and the prescription script, a first communicator connected to the benefit artifact, for communicating the benefit artifact to the pharmacy gateway, and a second communicator connected to the benefit artifact, for communicating the benefit artifact to the server computer. The server computer updates the eligibility database in response to receiving the benefit artifact from the second communicator of the benefit processor.

In other aspects of the embodiments, the system includes a follow-up coupon of the discount database, communicated by the server computer to the cell phone at the phone number via the carrier network, in response to receiving the prescription token.

In yet other aspects of the embodiments, the system includes a memory of the cell phone connected to the radio and the processor. The follow-up coupon is stored in the memory in response to receiving the follow-up coupon by the cell phone.

BRIEF DESCRIPTION OF THE DRAWINGS

The present invention is illustrated by way of example and not limitation in the accompanying figures, in which like references indicate similar elements, and in which.

DETAILED DESCRIPTION

Figure 1:
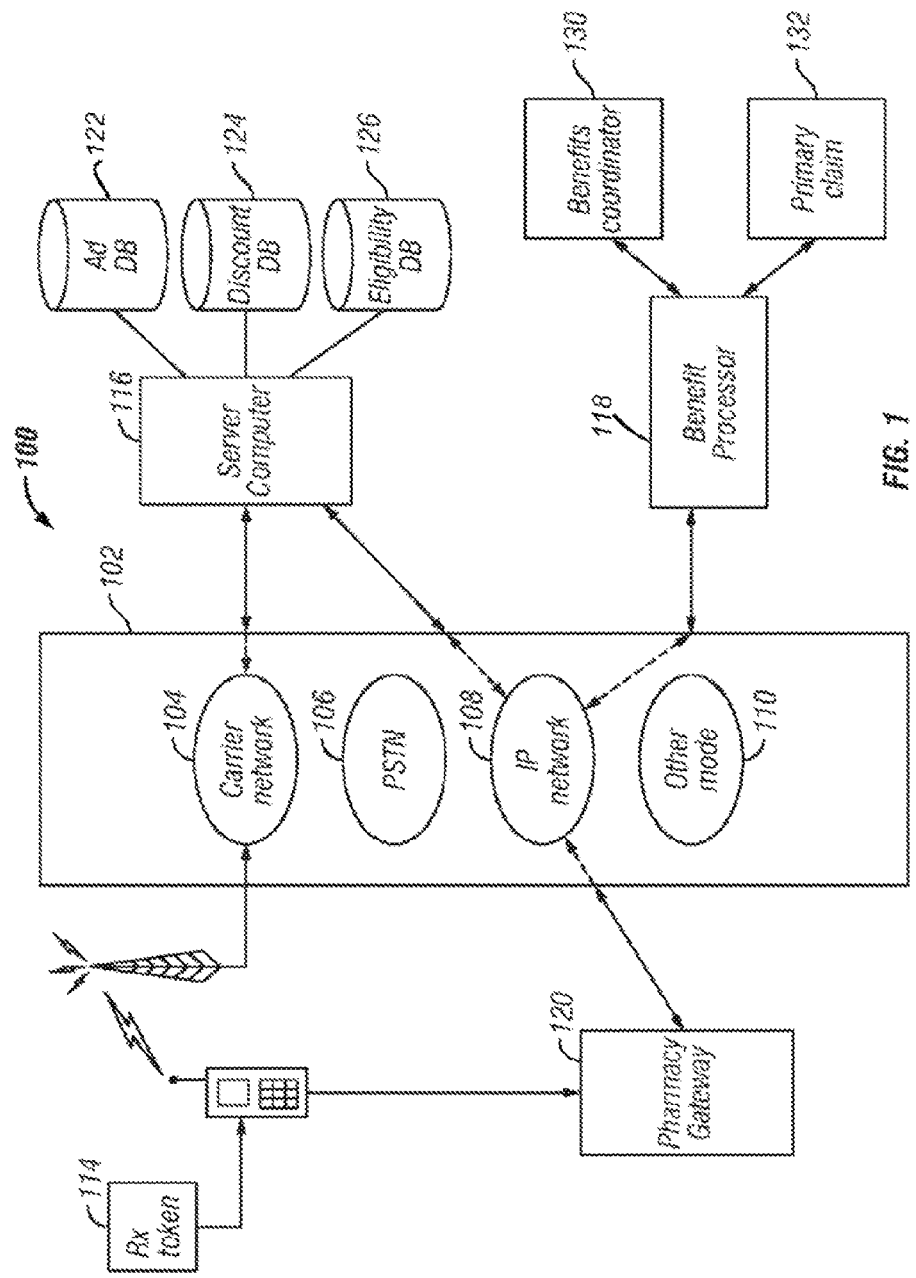
FIG. 1 illustrates a system for delivering a prescription drug discount to a cellular communications device over a cellular carrier network, according to certain embodiments of the invention.

Referring to FIG. 1, a system 100 for communicating with a prescription drug customer to provide drug discounts and aid drug therapy comprises one or more communications network 102. The network 102 includes a cellular carrier network (carrier network) 104, and can also include, for example, one or more of a public switched telephone network (PSTN) 106, a packet switched network (IP network) 108, and other channel or mode of communication 110. For convenience in discussion, the carrier network 104 is identified as such herein. Other communication networks, such as the PSTN 106, the IP network 108, and/or other channel or mode are sometimes individually or collectively referred to herein as "Other Networks." The term Other Networks, therefore, is intended to mean any one or more communications links which are not the carrier network 104. As will be understood, the carrier network 104, as well as the Other Networks, may be inter-linked or interconnected for communications between or among said networks or respective ones of them.

The system 100 also includes a cellular communications device 112. The cellular communications device 112 is communicatively connected to the carrier network 104. The cellular communications device 112 is any of a cellular radio transceiver capable of communicating messages, such as short message service (SMS), multimedia message service (MMS), enhanced message service (EMS), wireless access protocol service (WAP), and/or other message on the carrier network 104 to and from a destination serviced by the carrier network 104 and/or the Other Networks via communicative connection to the carrier network 104. Pluralities of the cellular communications device 112, as well as additional and varied types of cellular data, voice and information communicators, can concurrently communicatively connect to and communicate over the carrier network 104. For purposes of illustration in FIG. 1, the cellular communications device 112 is shown as a single unitized device; however, it is to be understood that the cellular communications device 112 may be any of a cellular telephone, cellular modem equipped laptop or personal digital assistant, similar cellular communicator, or a combination of any of these with other electronic device(s) and/or device components.

Figure 2:
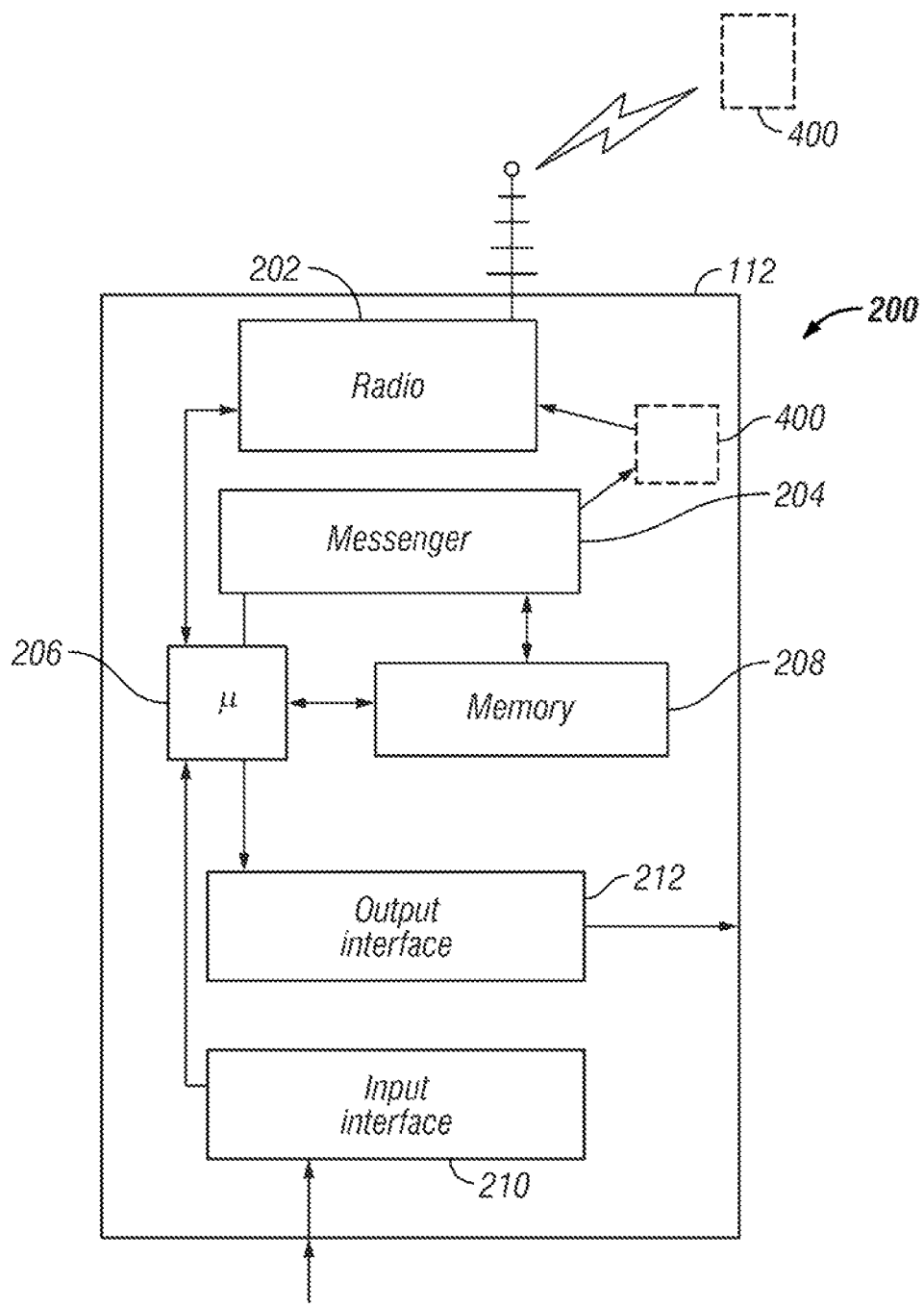
FIG. 2 illustrates an exemplary cellular communications device of the system of FIG. 1, according to certain embodiments of the invention.

Referring to FIG. 2, in conjunction with FIG. 1, the cellular communications device 112 of the system 100, for example, a cellular phone with messaging component(s), comprises a cellular radio 202, a messenger 204, a processor 206, a memory 208, an input interface 210 and an output interface 212. The processor 206 is connected to the messenger 204. The processor 206 is also connected to the memory 208, the input interface 210 and the output interface 212. The processor 206 can be a single microprocessor or other control circuit, or pluralities or combinations of these. The processor 206 controls the messenger 204, the memory 208, the input interface 210 and the output interface 210. The processor 206 can further be connected to the radio 202 for control of transmission and reception by the radio 202 on the carrier network 104. The messenger 204 is, for example, a microprocessor, logic circuit, messaging program stored in memory controlled by the processor 206, or pluralities or combinations, for initiating, creating, formatting, and transmitting, and receiving, constructing, transposing, and viewing, a cellular data message over the carrier network 104.

Figure 3:
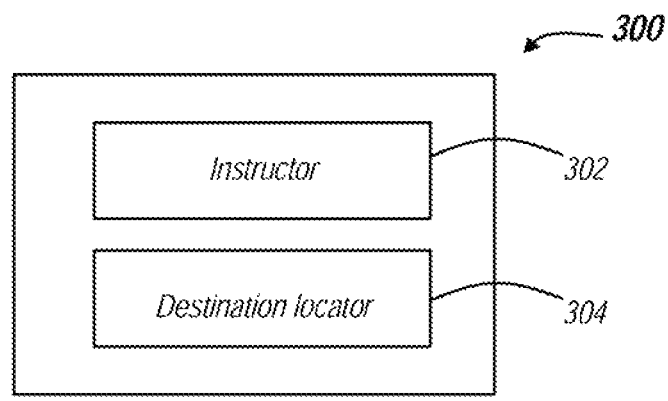
FIG. 3 illustrates a token structure of a prescription token of the system of FIG. 1, according to certain embodiments of the invention.

Referring to FIG. 3, in conjunction with FIGS. 1 and 2, the system 100 further comprises a prescription token (Rx token) 114 providing input to the cellular communications device 112. The Rx token 114 comprises a token structure 300, including at least one instructor 302 relative to the Rx token 114 and at least one destination locator 304 of the carrier network 104 (or of one of the Other Networks communicatively connected to the carrier network 104). The cellular communications device 112 processes the at least one instructor 302, such as upon input via the input interface 210, to generate the token structure 300 and store the token structure 300 in the memory 208. The at least one destination locator 304 targets the token structure 300 for communicative receipt by a server computer 116 (shown in FIG. 1) of the system 100. In addition to the at least one instructor 302 and the at least one destination locator 304, the token structure 400 can, but need not necessarily, comprise an authorization artifact, policy, or other article or component (not shown in detail in FIG. 3) of or for the Rx token 114.

The Rx token 114 is input to (or read or received by) the cellular communications device 112. For example, the Rx token 114, or representative features thereof, is entered to the input interface 210 of the cellular device 112, such as by a keypad, magnetic, infrared or radio frequency identification (RFID) reader, Bluetooth™ communicator or dongle, touch screen, or other interface component of the cellular communications device 112. Via the processor 206, in conjunction with the input interface 210 and the memory 208, as applicable, the token structure 300 of the Rx token 114 is saved in the memory 208. In certain embodiments, the Rx token 114 is a card, such as a plastic wallet card, representing the at least one instructor 302 and the destination address 304 provided to the user of the cellular device 112 for input by the user to the cellular device 112. Alternately, the Rx token 114 can be communicated to the cellular communications device 112 from an external source (not shown), via a communication interface (such as the radio 202 or another data input component) for message service, e-mail, website download, or via other component of the cellular communications device 112 capable of receiving such input. In other alternatives, the Rx token 114 can be pre-installed as an application or stored bits in programmed memory (e.g., ROM, EPROM, EEPROM) of the cellular communications device 112.

The Rx token 114 in certain embodiments is the token structure 300. As the token structure 300, the Rx token 114 is itself an input to, read into, and/or converted by the cellular communications device 112 to a communicative message artifact 400 transmitted by the cellular communications device 112 on the carrier network 104. Alternately, the token structure 300 is representative of the Rx token 114 but is not itself the Rx token 114. As an example, the Rx token 114 directs or activates an input to the cellular communication device 112 of the token structure 300, and the token structure 300 is thereby controlled by the Rx token 114. In such example, the Rx token 114 is not itself the token structure 300 input to the cellular communications device 112, and, in effect, is proxy for the token structure 300 as retained in the memory 208 of the cellular communication device 112.

Figure 4:
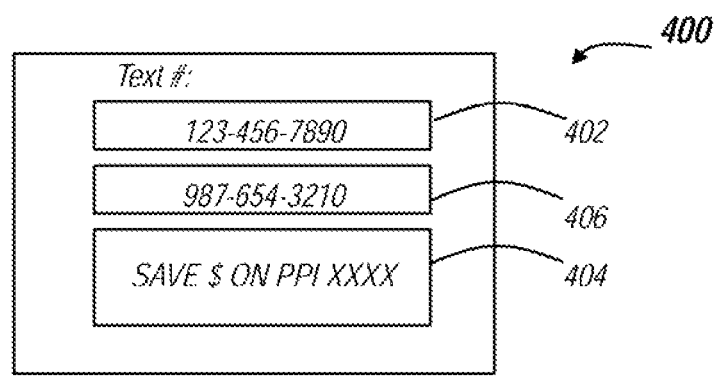
FIG. 4 illustrates a message artifact for the token structure of the system of FIG. 1, according to certain embodiments of the invention.

Referring to FIG. 4, in conjunction with FIGS. 1 and 2, the messenger 204, through operations of the processor 206 and the memory 208, processes and transforms the token structure 300 to create a message artifact 400 capable of communication by the cellular communications device 112 on the carrier network 104. The message artifact 400 comprises a destination address 402 of the network 102 for a receiver connected to the network 102, such as via the carrier network 104 or connected by the Other Networks to the carrier network 104.

The message artifact 400 also comprises a request segment 404. The message artifact 400 can additionally comprise, for example, a privacy policy, restriction policy, other policy, and/or directive or control (collectively, the "policy 406), for authorizing the cellular communications device 112 to use the Rx token 114 and to communicate the message artifact 400 on the carrier network 104. In certain embodiments, the message artifact 400 is a cellular message, such as short message service (SMS), multimedia message service (MMS), enhanced message service (EMS), wireless access protocol service (WAP), and/or other message transmittable by the cellular communications device 112 over the carrier network 104 to the destination address 402 of the network 102.

The request segment 404 of the message artifact 400 designates a particular prescription drug, such as digital bits representing "PPIxxxx", where "PPI" is an identifying nomenclature for the class of the prescription drug and "xxxx" is an index number of the particular make/type of the drug. The destination address 402 controls routing of the message artifact 400 when transmitted on the carrier network 104 (and any applicable intermediate or destination pathways of the Other Networks connected to the carrier network 104) to the destination address 402 of the network 102. The policy 406, if included in the message artifact 400, accompanies and relates to the request segment 402 and the destination address 404 to maintain verification, authorization, and/or integrity of delivery of the message artifact 400 at the destination address 402 on transmission by the cellular communications device 112.

Figure 5:
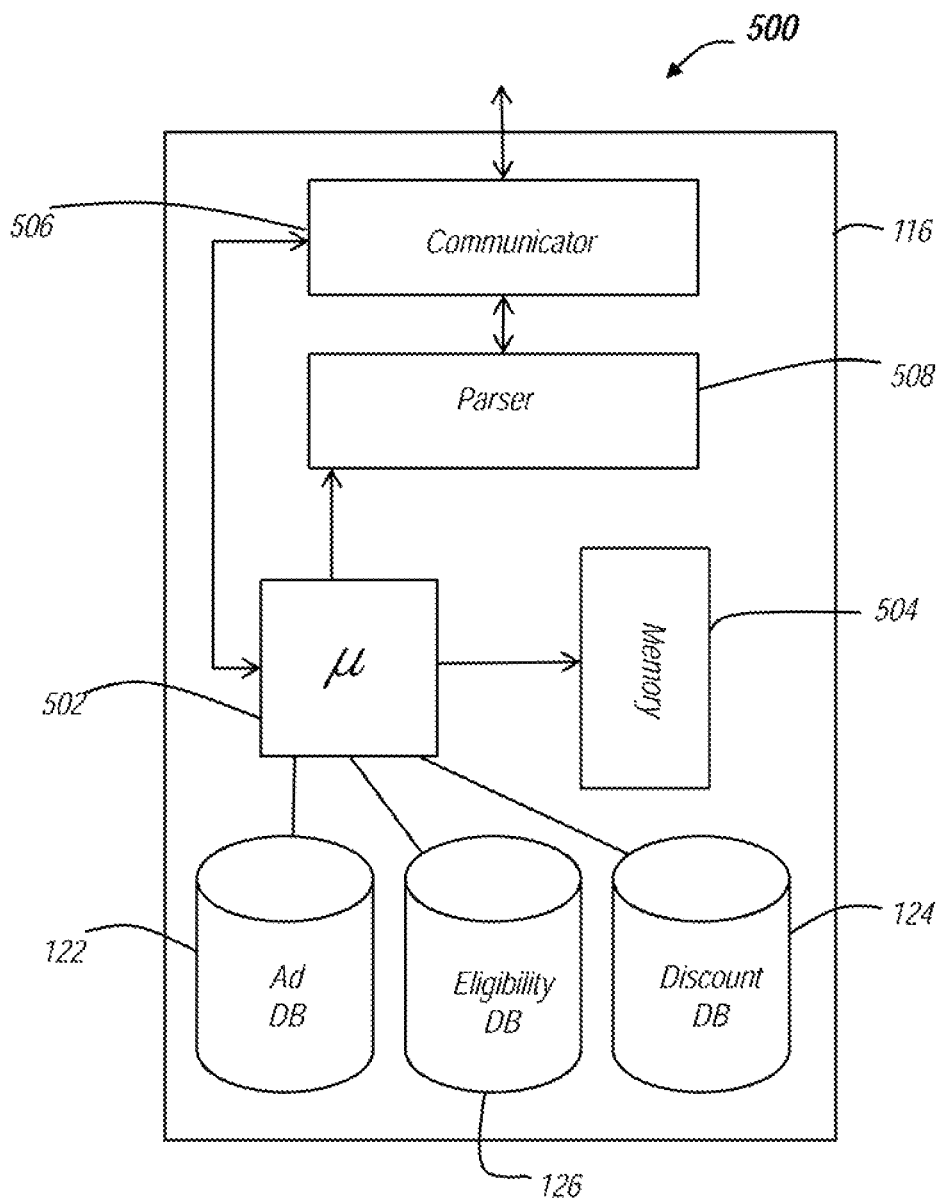
FIG. 5 illustrates an exemplary server computer of the system of FIG. 1, according to certain embodiments of the invention.

Referring to FIG. 5, in conjunction with FIG. 1, the server computer 116 of the system 100 is communicatively connected to the carrier network 104, directly or via one or more of the Other Networks communicatively connected to the carrier network 104. The server computer 116 has the destination address 404, such as by an IP address, cellular call number, or other communicative identifier of the server computer 116 on the network 102. The server computer 116 comprises a server processor 502, memory 504 connected to the server processor 502, at least one communicator device 506 connected to the server processor 502, and a message parser 508 connected to the at least one communicator device 506. The at least one communicator device 506 is a cellular modem, wired data connector (such as an Ethernet port), wireless data connector (such as a wireless area network (WLAN) modem), or other input/output component communicatively connected to the carrier network 104, directly or indirectly. The message parser 508 is a hardware component, software stored in memory, or combination, of the server computer 116 and can be or include the server processor 502.

The server computer 116 further comprises an ad processor 122, a discount processor 124 and an eligibility processor 126. Alternatively, the server computer 116 communicatively connects to at least certain of the ad processor 122, the discount processor 124 and/or the eligibility processor 126 external to the server computer 116. Each of the ad processor 122, the discount processor 124 and the eligibility processor 126 comprises or communicatively connects to a data processor, a memory, and a relational database stored in memory. In certain embodiments, the ad processor 122, the discount processor 124 and the eligibility processor 126 comprise at least certain of the processor 502, memory 504, and/or, if included in the server computer 116, one or more relational database (not shown in FIG. 5) stored in the memory 504.

Figure 6:
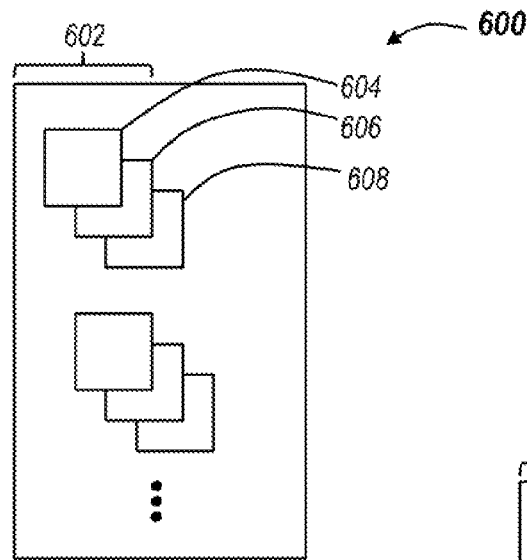
FIG. 6 illustrates an exemplary eligibility database of the server computer of the system of FIG. 1, according to certain embodiments of the invention.
Figure 7:
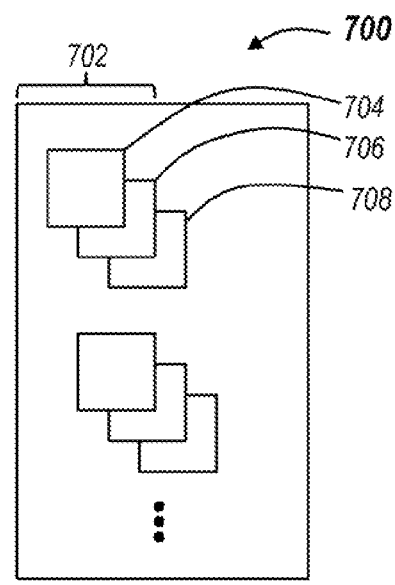
FIG. 7 illustrates an exemplary discount database of the server computer of the system of FIG. 1, according to certain embodiments of the invention.
Figure 8:
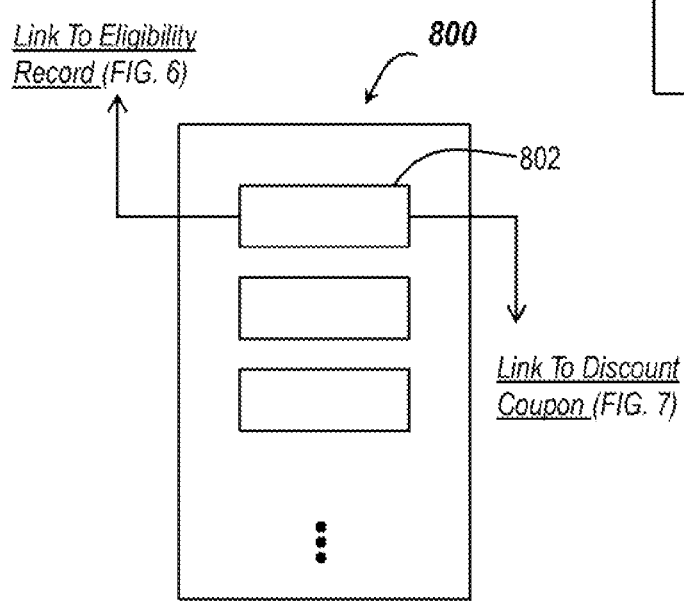
FIG. 8 illustrates an exemplary ad database of the server computer of the system of FIG. 1, according to certain embodiments of the invention.

Referring to FIGS. 6-8, in conjunction with FIGS. 1 and 5, the ad processor 122, the discount processor 124, and the eligibility processor 126, each comprise a processor, memory, and relational database stored in memory. Each database comprises at least one record and at least one field structure of each record. The database also comprises one or more logical relators for relationally associating each field structure with one or more records. Each field structure is (or points to) a respective data segment stored in memory. The data segment of each field structure can be any data, text, and/or logical operators, for example, a cellular phone identity (such as cell phone number), system opt-in permit, privacy policy, drug selector, transmit or receive message format, drug identifier, and other information bits. The database, operating via the processor and the memory, relationally organizes, and associates and selectively queries, sorts, filters, parses, retrieves, and reports, one or more of the data segments associated with applicable ones of the field structure. As will be appreciated, the ad database 122, the discount database 124 and the eligibility database 126 can comprise the same or different processor, memory and relational database stored in memory.

In exemplary embodiments, the respective relational database(s) of the eligibility processor 126 is illustrated in FIG. 6, of the discount database 124 is illustrated in FIG. 7, and of the ad database 122 is illustrated in FIG. 8. Referring to FIG. 6, the relational database 600 of the eligibility processor 126 comprises one or more eligibility records 602. Each of the eligibility records 602 comprises a cellular phone identity 604, a patient number 606, and an eligibility article 608. The phone identity 604 is relationally linked (i.e., associated) with the patient number 606, and the patient number 606 is relationally linked with the eligibility article 608.

Referring to FIG. 7, the relational database of the discount database 124 comprises one or more discount coupon 702. Each discount coupon 702 comprises a discount artifact 704, a pharmacy identity 706, and a drug unit 708. The pharmacy identity 706 is relationally linked to the drug unit 708. The discount artifact 704 is relationally linked to the drug unit 708 and, in certain embodiments, to the pharmacy identity 706. In certain embodiments, the discount artifact 704 is generated by the server processor 502 (of the server computer 116 of FIG. 1) via a program stored in memory (not shown in detail); for example, based on the drug unit 708, the pharmacy identity 706, and a particular one of the eligibility records 602, the discount program logically generates the discount artifact 704.

Referring to FIG. 8, the relational database of the ad database 122 comprises a plurality of ad messages 802. The ad messages 802 are relationally linked to the eligibility records 602 and the one or more discount coupon 702, either via processing by the server processor 502, via an ad program stored in memory (not shown in detail), by the eligibility processor 700 and discount processor 800, or combinations. Operations of the eligibility processor 126, the discount database 124, and the ad database 122 are later described in conjunction with operations of the server processor 502 and other aspects of the system 100.

Figure 9:
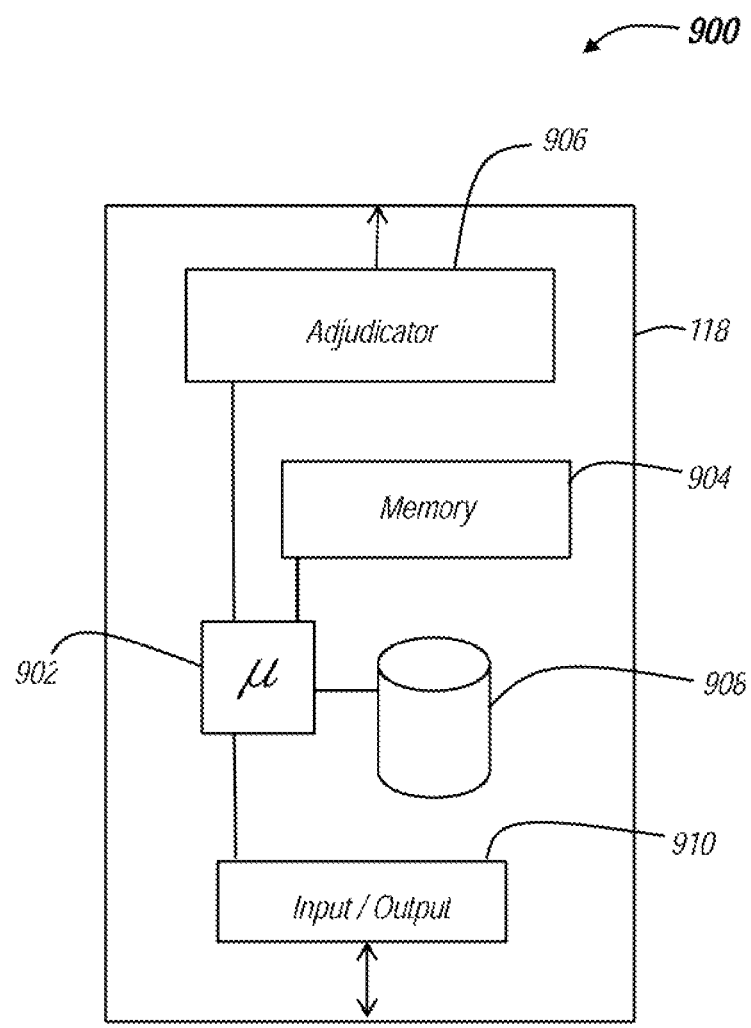
FIG. 9 illustrates an exemplary benefit processor of the system of FIG. 1, according to certain embodiments of the invention.

Referring to FIG. 9, in conjunction with FIG. 1, a benefit processor 118 comprises an input/output interface 910 communicatively connected, via one or more of the carrier network 104 and/or the Other Networks, to the server computer 116. In certain embodiments, the benefit processor 118 comprises a microprocessor 902, a benefit memory 904, an adjudicator 906, and a benefit database 908 stored in the benefit memory 1004. The microprocessor 902 connects to the input/output interface 910, the benefit database 908, the memory 904, and the adjudicator 906. The adjudicator 906 is, for example, a software program stored in memory or hardware logic component. In certain embodiments, the benefit processor 118 is a computer and the input/output interface 910 is a wired, wireless or cellular modem or other communicative element connected to the IP network 108 directly and/or, alternatively or in combination, indirectly via the network 102. In certain embodiments, the benefit processor 118 connects to the IP network 108 and communicates thereon with the server computer 116 via a web browser, file transfer protocol (ftp) or proprietary program stored in memory, proprietary protocol communicator, e-mail communicator, messaging system, electronic data interchange (EDI) system, or other device or connected component of the benefit processor 118.

The adjudicator 906 of the benefit processor 118 comprises, or is communicatively connected to, a benefits coordinator 130 and a primary claim negotiator 132. The benefits coordinator 130 and the primary claim negotiator 132 are each stores of insurance coverage data for patients obtaining prescription drugs via the system 100. An example of the benefit processor 118 is an insurance benefits processing company computer system or network and related database(s). In an exemplary embodiment, the benefits coordinator 130 administers Medicare prescription drug claims of patients and the primary claim negotiator 132 administers primary insurer prescription drug claims of patients.

Referring back to FIG. 1, a pharmacy gateway 120 communicatively connects, via network 102, to the benefit processor 118. The pharmacy gateway 120 is a computer, telephone, or other communicator device having one or more of a wired, wireless or cellular modem or analog voice transceiver communicative link to the benefit processor 118, for example, a local area network (LAN), a wireless area network (WLAN), enterprise sub-networks, router, switch, computer, the cellular network 104, the PSTN 106, the other channel or mode 110, switchboard, private branch exchange system, portions or sub-networks thereof, and other links. In certain embodiments, the pharmacy gateway 120 connects to the IP network 108 for communications with the benefit processor 118. The pharmacy gateway 120 in certain embodiments communicatively connects to the cellular communications device 112 via the carrier network 104. In alternate embodiments, the pharmacy gateway 120 communicates with the cellular communications device 112 by viewing a display of the cellular communications device 112, reading a file structure of the cellular device 112, communicating with the server computer 116 as proxy for the cellular communications device 112 (such as on the IP network 108 or the Other Networks), or via cellular or analog telephone call of the cellular communications device 112 or other device (not shown in detail).

In operation of the system 100, the token structure 300 of the Rx token 114 is captured to the memory 208 of the cellular communications device 112, such as via signal input to the input interface 210 of the cellular communications device 112 or as otherwise previously described. The processor 206 stores the token structure 300 in the memory 208. The messenger 204 is then initiated, and in conjunction with operations of the processor 206 and the memory 208, creates the message artifact 400 from the token structure 300. The messenger 204, in conjunction with the processor 206, controls the radio 202 to transmit the message artifact 400 to the destination address 402 for the server computer 116 over the carrier network 104.

In certain embodiments, upon capture of the token structure 300 of the Rx token 114 and further direction input to the input interface 210 of the cellular communications device 112, the messenger 204 is initiated by the processor 206 in response to signal of the input interface 210 (e.g., initiation of operations of the messenger 204 as an application program stored in memory via signal of the input interface 210). For example, a user of the cellular communications device 112 initiates the messenger 204 by instruction entry to the input interface 210. In other embodiments, the messenger 204 is initiated automatically on receipt or storage of the token structure 300 in the memory 208, or otherwise.

The messenger 204, under control of the processor 206, delivers the message artifact 400 to the radio 202 of the cellular communications device 112. The radio 202 transmits the message artifact 400 as a cellular message on the carrier network 104.

The server computer 116 receives the message artifact 400 sent by the cellular communications device 112 from the network 102 via the communicator 506. As received, the message artifact 400 is constructed and parsed by the server computer 116 for the token structure 300. The token structure 300, or portions, is saved in the server memory 504.

The server processor 502 of the server computer 116 performs a look-up in the eligibility database 126 for any of the eligibility records 602 containing (or otherwise relevant) to the token structure 300. For example, the server processor 502 filters the eligibility records 602 to determine if the at least one instructor 302, or portions, of the token structure 300 match any cellular phone identity 604 of the eligibility records 602. If match is not found, the server processor 502, in conjunction with the eligibility database 126 creates a new one of the eligibility records 602 for the cellular phone identity 604 and other details of the token structure 300 (i.e., in such instance, the created eligibility record is for a new patient/user with a cell phone not recognized as previously registered with the system). The server processor 502 then performs a look-up in the discount database 124 to retrieve the discount coupon 702 for the new eligibility record 602 created for the cellular phone identity 604. The discount coupon 702 comprises the discount artifact 704, the pharmacy identity 706 and the drug unit 708. For example, the discount coupon 702 obtained from the look-up provides information of a particular pharmacy and saving discount. The server computer 116 sends the discount coupon 702, as a message (e.g., SMS, MMS, EHS, WAP, or other message), to the cellular communications device 112 (either directly on the carrier network 104 or via the Other Networks communicatively connected to the carrier network 104). If, however, match is found in the look-up by the server computer 116 in the eligibility database 126 (e.g., the cellular phone identity 604 is present in at least one of the eligibility records, indicating a previously registered patient/user with a cell phone recognized as previously registered with the system), the applicable eligibility record(s) 602 for the at least one instructor 302 are retrieved by the server processor 502. The discount database 124 is then searched to determine the applicable discount coupon 702 relevant to the particular instructor 602 and eligibility record(s) 602. The server computer 116 then sends the discount coupon 702, as a message on the network 102, to the cellular communications device 112 for receipt from the carrier network 104.

After the applicable discount coupon 702 is sent as the message by the server computer 116, the messenger 204 of the cellular communications device 112 receives the discount coupon 702 over the carrier network 102. The processor 206 of the cellular communications device 112 processes and displays output via the output interface 212 representing the discount coupon 702. The discount coupon 702 is saved in the memory 208, either automatically on processing and display or by instruction to the input interface 210.

By direction to the input interface 210 by the user of the cellular communications device 112, the discount coupon 702 is presented to the pharmacy gateway 120. Delivery of the discount coupon 702 is, for example, via viewing of a display representing the discount coupon 702 on the cellular communications device 112 at the physical location of a pharmacy, communicative transmission of the discount coupon 702 by the cellular communications device 112 to the pharmacy gateway 120, such as over the carrier network 104, or communicative transmission of the discount coupon 702 to the pharmacy gateway 120 via one of the Other Networks, either by the cellular communications device 112 or another networked device.

On presentation of the discount coupon 702 to the pharmacy gateway 120, the pharmacy gateway 120 communicates to the benefit processor 118 the discount coupon 702, together with a prescription script corresponding to the discount coupon 702, applicable identifier for the drug of the prescription script (obtained by the patient from a physician), an identifier of the patient relevant to the prescription script, and other items (such as may be required by the benefit processor 118). The benefit processor 118 receives the communication, and processes a covered benefit related thereto. In processing the covered benefit, the adjudicator 906 of the benefit processor 118 accesses the benefits coordinator 130 and/or the primary claim negotiator 132. If the covered benefit is available from the benefits coordinator 130, then the benefit processor 118 communicates a coverage indicator to the pharmacy gateway 120. If the covered benefit is not available from the benefits coordinator 130, then the benefit processor 118 communicates a no coverage indicator to the pharmacy gateway 120.

If the pharmacy gateway 120 gateway receives a coverage indicator, then the pharmacy processes the prescription in typical manner, provides the patient a discount per the discount coupon 702, and charges the patient a price for the prescription reduced by the discount and the covered benefit. If the pharmacy gateway 120 receives a no coverage indicator, then the pharmacy processes the prescription in typical manner, provides the patient the discount per the discount coupon 702, and charges the patient a price for the prescription reduced by solely the discount.

Upon the benefit processor 118 communicating the coverage indicator or no coverage indicator to the pharmacy, the benefit processor 118 communicates to the server computer 116 an eligibility update notification. The eligibility update notification is received by the server computer 116, processed and stored in memory. The server processor 502 controls the eligibility processor 126 to change the eligibility records 602 for the patient number, for example, per a particular patient number 606 of the patient (as indicated by the eligibility update notification), corresponding to the particular prescription, such as by storing in memory a different eligibility status indicator in the relationally linked eligibility article 608 of the applicable eligibility record(s) 602.

These operations of the system 100 are repeated for each next Rx token 114 captured in and transmitted by the cellular communications device 112, with the result that each next Rx token 114 will result in change to the cellular communications device 112, the server computer 116, and the benefit processor 118 reflecting each prescription transaction by a patient associated with the particular cellular communications device 112.

Figure 10:
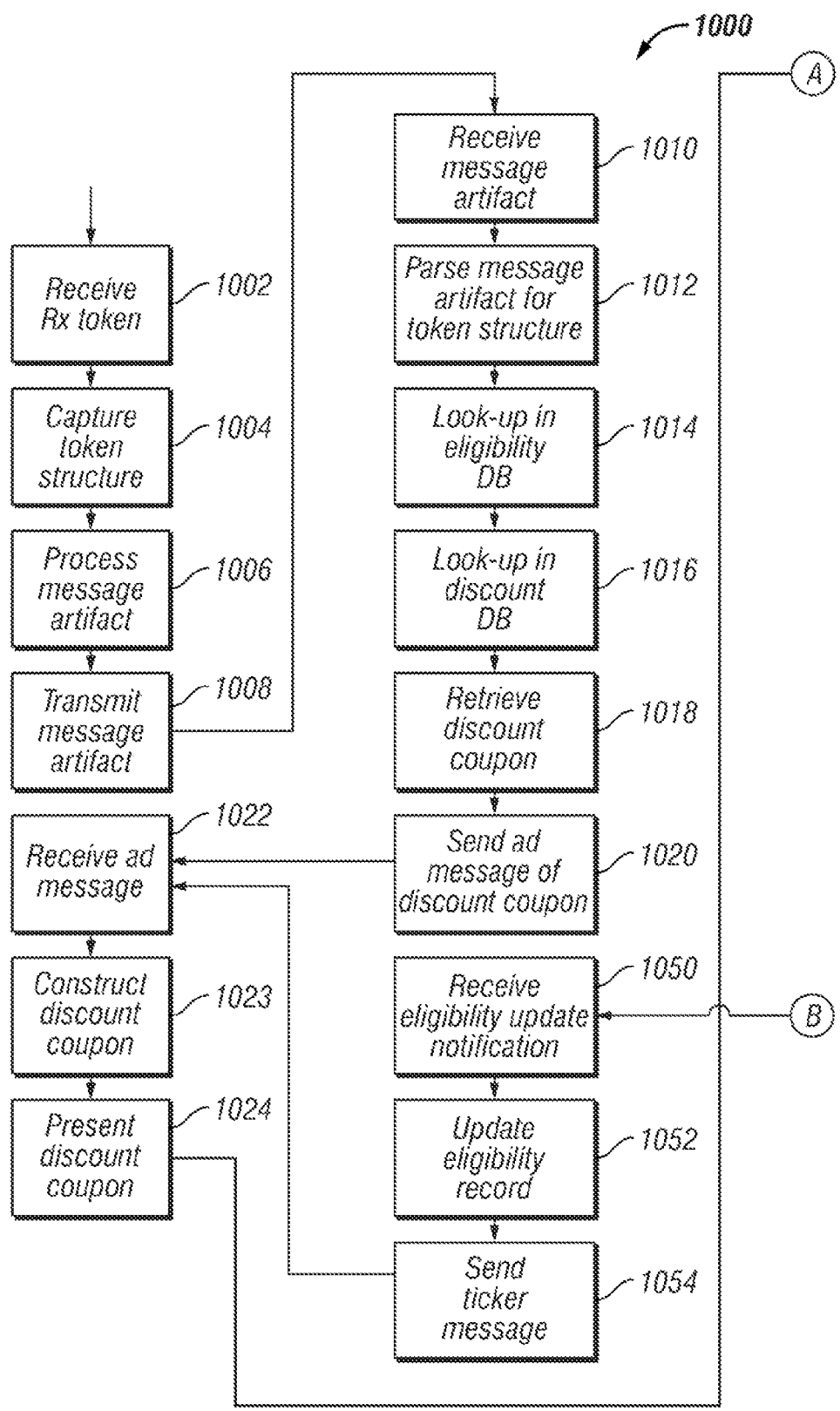
FIG. 10 illustrates a method of delivering a prescription drug discount to a cellular communications device over a cellular carrier network, according to certain embodiments of the invention.
Figure 10:
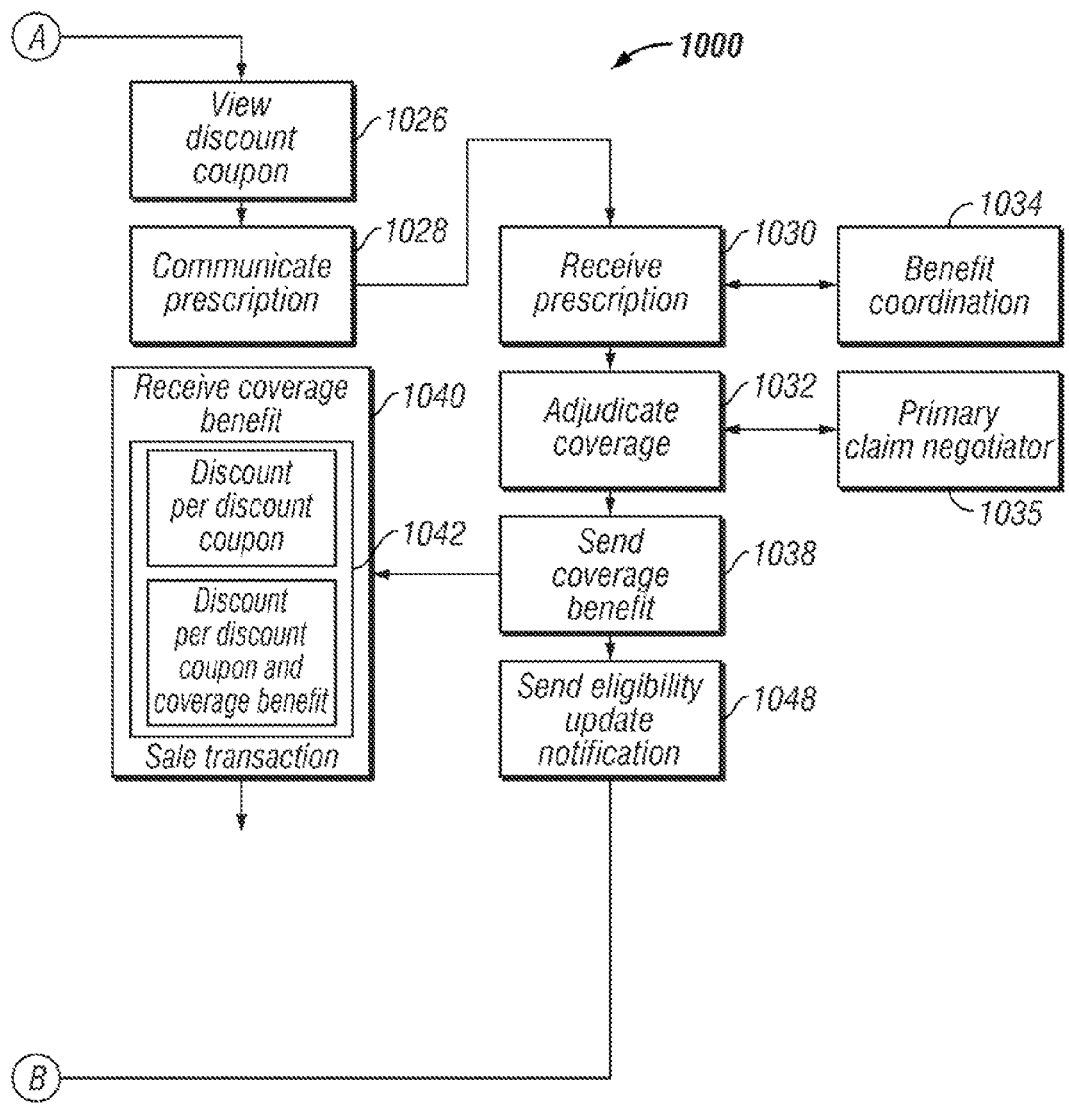

Referring to FIG. 10, a method 1000 of communicating with a prescription drug customer to provide drug discounts and aid drug therapy comprises a step 1002 of receiving the Rx token 114 by a user of a cellular communications device 112. For example, the Rx token 114 is obtained by a patient from a physician, together with a prescription script for a drug addressing the patient's malady. The token structure 300 of the Rx token 200 is input to the input interface 210 or otherwise captured in the memory 208 of the cellular communications device 112 in a step 1004. The cellular communications device 112 is, for example, a cell phone of the patient or care-provider of the patient.

In a step 1006, the messenger 204 is initiated, such as by additional direction input to the input interface 210 or storage of the token structure 300 in memory 208, and the processor 206 of the cellular communications device 112 processes the token structure 300 to generate the message artifact 400 in respect of the token structure 300. The message artifact 400 is transmitted by the radio 202, under direction of the memory 208 and control of the processor 202, on the carrier network 104. The message artifact 400 is, for example, a cellular message transmitted by the cellular communications device 112, such as an SMS, MMS, EMS, WAP, or other message, directed to the destination address 402 of the network 102 for the server computer 116.

In a step 1010, the server computer 116 receives the message artifact 400 as communicated to the server computer 116 by the network 102. The network 102 can be the carrier network 104, or another of the Other Networks communicatively connected to the carrier network 104. On receipt of the message artifact 400 by the server computer 116, the message parser 508 of the server computer 116 constructs, parses and translates the message artifact 400 to recover the token structure 300 in a step 1012.

The server computer 116 performs a logical look-up in a step 1014 of an aspect of the token structure 300 in the eligibility database 126. In the step 1014, the eligibility records 602 are filtered to determine any match to the at least one instructor 302, or portions, of the token structure 300. For example, the at least one instructor 302 of the token structure 300 includes the cellular phone identity 604, such as cell phone number for the cellular communications device 112 and a designation for particular prescription drug of the prescription script provided by the physician to the patient-user of the cellular communications device 112. In certain embodiments, the at least one instructor 302 includes a message, such as "Save $ on PPIxxxx" where PPIxxxx identifies the class and particular make/type of drug of the prescription script.

The server computer 116 performs a next logical look-up in a step 1016 of the discount coupon 702 applicable to the prescription drug (such as PPIxxxx) and particular eligibility records 602, if any, located in the step 1014. If none of the eligibility records 602 are located in the step 1014, the server computer 116, in a step 1018, retrieves the ad message(s) 802 for the particular discount coupon 702 of the step 1014. If eligibility records are located in the step 1014, the server computer 116 in the step 1018, instead, retrieves a different one or more of the ad message 802 for the discount coupon 702 of the step 1014. In a step 1020, the server computer 116 sends the ad message 802 retrieved in the step 1018, for receipt by the cellular communications device 112 over the carrier network 104. For example, in the step 1020, the server computer 116 sends the ad message 802 on the network 102, such as by an SMS, MMS, EMS, WAP or other message, to the phone number for the cellular communications device 112.

The cellular communications device 112 receives the ad message 802 in a step 1022. In a step 1023, the ad message 802 is constructed, parsed, saved and displayed by the cellular communications device 112 in the form of the discount coupon 702. In a step 1024, the user of the cellular communications device 112 presents the discount coupon 702, together with the prescription script, to a pharmacy. The presenting step 1024 comprises, for example, display of the discount coupon 702 on the cellular communications device 112 at the physical location of the pharmacy (e.g., the cellular communications device 112 is carried to the pharmacy and the discount coupon 702 is shown to a pharmacist via the output interface 212), transfer of the discount coupon 702 to the pharmacy gateway 120 for receipt by the pharmacy (e.g., the cellular communications device 112 communicates the discount coupon 702 to the pharmacy gateway 120 by cellular message, website upload, ftp transfer, or other), or other mode (e.g., the discount coupon 702 is delivered to the pharmacy gateway by another network device, such as a networked computer, capable of communicating on the network 100, the discount coupon 702 is printed from the cellular communications device 112 and the print copy is given to the pharmacy, or otherwise).

On presentation of the discount coupon 702 in the step 1024, the pharmacy gateway 120 (or pharmacy, as applicable) views the discount coupon 702 in a step 1026. The pharmacy gateway 120, in a step 1028, communicates the prescription script to the benefit processor 118, together with identification of the applicable patient and any additional information required by the benefit processor 118. For example, the pharmacy gateway 120 communicates in the step 1028 via the network 102, with the benefit processor 118.

In a step 1030, the benefit processor 118 receives the prescription script, together with the additional information. The benefit processor 118 adjudicates the coverage benefit applicable to the prescription script and patient in a step 1032. The step of adjudicating 1032 the coverage benefit includes either: a step of communicating 1034 with the benefits coordinator 130 if the benefits coordinator 130 provides the coverage benefit, a step of communicating 1036 with the primary claim negotiator 132 if the benefits coordinator 130 does not provide the coverage benefit, or combination. In response to the step of adjudicating 1032, the benefit processor 118, in a step 1038, determines the coverage indicator/no coverage indicator, in respect of the coverage benefit from the step of adjudicating 1032, and communicates the coverage indicator or otherwise, the no coverage indicator, to the pharmacy gateway 120 (or pharmacy, depending on mode of communication).

In a step 1040, the pharmacy gateway 120 (or pharmacy, as applicable) receives the coverage indicator or no coverage indicator, as applies. If the pharmacy gateway 120 receives the coverage indicator, the pharmacy gateway 120 (or pharmacy) in a step 1042 provides the patient a discount in price, per the discount coupon 702, and less the coverage benefit per the coverage indicator, in a sale transaction of the prescription drug according to the prescription script. If, on the other hand, the pharmacy gateway 120 receives the no coverage indicator, the pharmacy gateway 120 (or pharmacy) in the step 1042 provides the patient a discount in price, per the discount coupon 702 (without any coverage benefit reduction), in a sale transaction of the prescription drug according to the prescription script.

On completion of the step 1038 by the benefit processor 118, the benefit processor 118 communicates the eligibility update notification to the server computer 118 in a step 1048. The server computer 118 receives the eligibility update notification in a step 1050. Communication of the eligibility update notification is via the network 102. Upon the receiving step 1050, the eligibility update notification is read by the server computer 118. In a step 1052, the server processor 502, in response to the eligibility update notification, controls the eligibility processor 126 to change the eligibility records 602 stored in memory, for the patient number 606 corresponding to the eligibility update notification and prescription. For example, an eligibility status indicator in the related eligibility article 608 of the eligibility records 602 is modified to evidence that the sale transaction was completed for the prescription drug, with the applicable discount in price (i.e., either per discount coupon and coverage benefit reduction, if covered benefit; or per discount coupon, if no covered benefit).

The server computer, thereafter, in a step 1054, based on the eligibility records 602 as then existing for each respective patient number 606 and eligibility article 608, can send ticker reminder messages to the cellular communications device 112. In the step 1048, for example, the eligibility records 602 are periodically (e.g., daily) filtered and processed under control of the eligibility processor 126, to detect date(s) when refills of the prescription drug (and/or related or other products or services) would be needed by the relevant patient. In the step 1054, a ticker reminder message is sent to the cellular communications device 112 associated with the relevant patient per the cellular phone identity 604 of the eligibility records 602. The ticker reminder message is an SMS, MMS, EMS, WAP or other cellular message, sent by the server computer 116 on the network 102 directed to the carrier network 104, for receipt from the carrier network 104 by the cellular communications device 112 of the relevant patient.

Various alternatives and additions are possible in the foregoing embodiments. In certain alternatives, the discount per the discount coupon 702 may be provided by other than the pharmacy, such as by an insurer (e.g., to encourage patient participation and compliance to drug therapy regimen), a physician (e.g., to advertise), a pharmacy-related entity (e.g., to advertise products or services available at the pharmacy in addition to the prescription drug), and others. The discount coupon 702 can relate to a discount associated with any device or entity of the system or any other or external source. The server computer 116 or related discount database 126, alternatively, can be managed or provided by an external device or network to the system 100, such as by an input to the system 100. In certain alternatives, the benefit processor 118 and pharmacy gateway 120 are not included in the system 100, and/or the server computer 116 provides the functionalities of the benefit processor 118 and the pharmacy gateway 120. An example of such scenario is a pharmacy conglomerate or pharmacy/insurer combination which provides the functionalities of the server computer 116, benefit processor 118 and pharmacy gateway 120 either directly without the network 102 or via other modes and devices.

In other alternatives, modifications and additions, the system 100 permits advertising, via the pharmacy gateway 120, the server computer 116, and/or benefit processor 118, based on the eligibility records 602 or other elements of the system 100. For example, the eligibility records 602 can provide information and data of distinct patients (or communication devices of or related to those patients). Accumulation of such information and data in the manner of targeted cellular message communications from the patient to a particular destination of the network, and security protected channels of communications between pharmacy and benefit providers, affords security of communications of patient information and, yet, allows for targeted advertising delivery to the patient by such secure channels. Through communicative connection to the eligibility records 602, any authorized device can direct or control the discount database 124, such as to make available particular form of the discount coupon 702 (and thus the discount, for example, if pricing changes, new discount items are advertised, etc.). Similarly, the server computer 116 can be controlled through such communicative connection, such as to send cellular messages to the cellular communications device 112 alerting to additional items, with directed timing or other criteria.

An example implementation of the foregoing embodiments follows:

A physician writes a prescription script and provides the patient with the script and a Rx token. The Rx token includes, for example, a HIPAA/privacy disclaimer and directions for input to a cellular phone of the patient. The patient inputs a token structure to the cell phone and commences a messenger of the cell phone to create a text message according to the directions of the Rx token and representing the token structure. The text message is an SMS message for transmission by the cellular phone on the cellular carrier network servicing the phone. The text message, per the directions, includes the text "Save $ on PPIxxxx" and is transmitted to a phone number xxx-xxx-xxxx per the directions.

The text message is received over a network, either the cellular carrier network or another network connected to the cellular carrier network, at the phone number (or at a designated location of the network, such as IP address, at which the message is proxied to the phone number). The text message is interpreted by a savings manager center, such as a server computer. The savings manager center searches database(s) records relevant to the received message, and responds to the cell phone via the cell phone number, with a response text message. This response text message includes a direction for a particular pharmacy, pharmacy instructions, and patient reference, such as "To save $ now, have [Pharmacy ABC] submit prescription drug claim to BIN XXXXXX & Group# PP125 with ID# YM12345. Usage constitutes opt-in for follow-up" (e.g., 132 characters). This response text message is delivered by the cellular carrier network to the cell phone (or, in certain scenarios, the message is maintained by a message center accessible to the cell phone).

The cell phone receives the text message from the savings manager center. The patient (or care-giver, etc.) then presents the pharmacy (i.e., Pharmacy ABC) with the text message received on the cell phone, together with the prescription script obtained from the physician. The pharmacy views the text message, such as via the cell phone display, and the pharmacy submits the prescription to a benefit processor (such as a Coordinator of Benefits, primary insurer, or other) for adjudication of benefit coverage applicable to the patient and prescription of the prescription script. The benefit processor adjudicates the prescription benefit coverage with a benefits coordinator of Medicare, if applicable, and/or a primary insurer, as may apply. If the prescription is covered by Medicare, the benefit processor processes the claim to buy down the patient's co-pay to $XX with a maximum benefit of $XX. If the prescription is not covered or only partially covered by Medicare, the benefit processor processes the claim under primary insurance coverage for a cash paying patient (or as rejected under Medicare as Drug Not Covered (70) or Prior Authorization Required (75)).

On adjudication by the benefit processor, the benefit processor communicates the applicable benefit coverage to the pharmacy. The benefit processor additionally sends details of the prescription benefit coverage and adjudication to the savings manager center. The details communicated to the savings manager center contain NCPDP (National Council for Prescription Drug Program) fields, as follows: Patient or Cardholder First Name, Patient or Cardholder Last Name, Patient or Cardholder Date of Birth, Patient or Cardholder Gender, Prescriber ID, Insurer ID, Primary CoPay, Pharmacy ID, COB (Coordination of Benefits, i.e., Medicare) indicator/value, NDC (National Drug Code) #, Quantity Dispensed, and Days Supply.

The savings manager center, based on these received details, creates and sends a follow-up text message to the cellular phone of the patient. If prescription benefit coverage has been successfully adjudicated through the benefits coordinator of Medicare, the follow-up text message includes a compliance message on 50% utilization of maximum benefit, such as "For additional Rx savings, please visit website www.textRxSavings.com to complete a survey about PPIxxxx." If, on the other hand, the prescription is not covered by Medicare, the follow-up text message includes direction to send a prior authorization inquiry immediately, such as "No plan coverage for PPIxxxx. If insurance denied PPIxxxx, we want to help. Text plan name to request coverage or none if no Rx plan" (e.g., 132 characters). On receiving the follow-up text message on the cellular phone of the patient, the patient views the message and takes subsequent action. For example, as directed by the follow-up message, the patient can visit the listed website or send a text message to the savings manager center.

The savings manager center additionally, based on the details received from the benefit processor, updates eligibility records for the particular patient, prescription, cellular phone identity/number and any other applicable modifications. The savings manager center communicates the update by the savings manager center to the benefit processor to provide additional benefit coverage discount. In response to the communication, the benefit processor updates a benefit database to register that a benefit is extended for a certain number of refills of the prescription, for a specific time period, and/or for a specified total dollar benefit. The update to the benefit database is thereafter reflected for the adjudication of any next prescription drug coverage in connection with refill, new prescription, or as otherwise applicable for the particular patient.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and device(s), connection(s) and element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method of delivering a purchase discount to a communications device, the communications device capable of capturing and sending over a telecommunications network a token representing a purchasable item associated with the purchase discount, comprising:

receiving the token by a server computer from the communications device over the telecommunications network;

looking-up in an eligibility database by the server computer at least a portion of the token;
obtaining at least one eligibility record from the step of looking-up in the eligibility database;
looking-up in a discount database by the server computer at least a portion of the at least one eligibility record;
obtaining at least one discount artifact from the step of looking-up in the discount database;
sending a discount coupon corresponding to the at least one discount artifact by the server computer over the telecommunications network to the communications device, the discount coupon representing the purchase discount; and
discounting price of the purchasable item associated with the purchase discount upon presentation of the discount coupon via the communications device.

2. The method of claim 1, further comprising:
sending a request for permission to the communications device over the telecommunications network by the server computer;
receiving a permission, in response to the step of sending the request, by the server computer over the telecommunications network from the communications device; and
saving the permission in the eligibility database by the server computer.

3. The method of claim 2, wherein the steps of sending the request for permission, receiving the permission, and saving the permission if not previously performed for the communications device, must precede the steps of looking-up in the eligibility database, obtaining the at least one eligibility record, looking-up in the discount database, obtaining the at least one discount artifact, sending the discount coupon, and discounting the price.

4. The method of claim 3, wherein the permission of the steps of sending the request, receiving the permission, and saving the permission is selected from the group consisting of: legal authorization, privacy authorization, medical authorization, restriction authorization, policy authorization, other directive, and any combination of any of these.

5. The method of claim 3, further comprising:
creating an eligibility record in the eligibility database for the communications device after the step of looking-up in the eligibility database, if the eligibility database does not then contain at least one eligibility record corresponding to the communications device from the step of looking-up in the eligibility database.

6. The method of claim 3, further comprising:
processing a coverage benefit associated with the purchasable item, based on the at least one eligibility record;
applying the coverage benefit of the step of processing for purchase of the purchasable item;
updating at least a portion of the at least one eligibility record after the step of applying.

7. The method of claim 3, wherein the communications device is a wireless device.

8. The method of claim 3, wherein the purchasable item includes a prescription drug, the purchase discount corresponds to the prescription drug, and the coverage benefit is an insurance benefit.

9. The method of claim 6, further comprising:
communicating an identifier of the purchasable item to a benefit provider; and
adjudicating the coverage benefit with the benefit provider.

10. The method of claim 7, wherein the wireless device is selected from the group consisting of: a messaging enabled cellular telephone, another cellular messaging device, a web-browser computer, another web-browsing device, and any combination of any of these.

11. A system for delivering a purchase discount to a communications device, the communications device capable of capturing and sending over a telecommunications network a token representing a purchasable item associated with the purchase discount, comprising:
a server computer for receiving the token from the communications device over the telecommunications network;
an eligibility database communicatively connected to the server computer, the eligibility database includes at least one eligibility record corresponding to the token;
a discount database communicatively connected to the server computer, the discount database includes a discount artifact corresponding to the at least one eligibility record corresponding to the token;
a discount coupon created by the server computer based on the discount artifact and communicated by the server computer over the telecommunications network to the communications device, the discount coupon representing the purchase discount applied on purchase of the purchasable item.

12. The system of claim 11, further comprising:
a permission request corresponding to the communications device created by the server computer, the server computer sends the permission request to the communications device over the telecommunications network; and
a permission corresponding to the permission request, received by the server computer over the telecommunications network responsive to the permission request and saved by the server computer in the eligibility database relative to the at least one eligibility record corresponding to the token.

13. The system of claim 12, wherein the permission is required by the server computer for creating the discount coupon.

14. The system of claim 12, wherein the permission is selected from the group consisting of: legal authorization, privacy authorization, medical authorization, restriction authorization, policy authorization, other directive, and any combination of any of these.

15. The system of claim 12, further comprising:
an eligibility record of the eligibility database created by the server computer for the communications device, if the eligibility database does not then contain at least one eligibility record corresponding to the communications device.

16. The system of claim 12, further comprising:
a coverage benefit of the at least one eligibility record, the coverage benefit corresponding to the purchasable item; and
wherein the at least one eligibility record is updated by the server computer relative to the coverage benefit if the purchasable item is purchased by applying the coverage benefit.

17. The system of claim 12, wherein the communications device is a wireless device.

18. The system of claim 12, wherein the purchasable item includes a prescription drug, the purchase discount corresponds to the prescription drug, and the coverage benefit is an insurance benefit.

19. The system of claim 16, further comprising:
an identifier representing the purchasable item, received by the server computer over the telecommunications network;

wherein the server computer communicates the identifier over the telecommunications network to adjudicate the coverage benefit.

20. The method of claim 19, wherein the wireless device is selected from the group consisting of: a messaging enabled cellular telephone, another cellular messaging device, a web-browser computer, another web-browsing device, and any combination of any of these.

21. A method of delivering a discount to a purchase price of a prescription drug via a cellular message on a cellular carrier network, comprising:
   receiving a prescription token and a drug identifier from a cellular communication device, by a server computer at a destination address of the server computer communicatively accessible by the cellular carrier network;
   looking-up at least a portion of the prescription token in an eligibility database communicatively connected to the server computer, the eligibility database comprises at least one eligibility record related to the prescription token, the drug identifier, and the cellular communication device;
   retrieving the at least one eligibility record by the server computer, from the step of looking-up at least the portion of the prescription token;
   looking-up at least a portion of the at least one eligibility record in a discount database communicatively connected to the server computer, the discount database comprises at least one discount artifact related to the drug identifier and the at least the portion of the at least one eligibility record;
   retrieving the at least one discount artifact of the discount database by the server computer, from the step of looking-up the at least the portion of the at least one eligibility record;
   generating by the server computer the cellular message representing a discount coupon;
   transmitting the cellular message by the server computer for receipt by the cellular communication device from the cellular carrier network; and
   providing the purchase price discount as per the discount coupon upon presentation of the cellular message by the cellular communication device and purchase of the prescription drug, the discount coupon represents a purchase price discount to the purchase price of the prescription drug.

22. The method of claim 21, further comprising:
   sending an authorization request by the server computer for receipt by the cellular communication device, if the at least one eligibility record is not found in the step of looking-up at least the portion of the prescription token after the step of receiving the prescription token and the drug identifier;
   receiving an authorization permission by the server computer from the cellular communication device; and
   creating the at least one eligibility record of the eligibility database corresponding to the cellular communication device and the authorization permission, upon the step of receiving the authorization permission.

23. The method of claim 21, further comprising:
   determining a coverage benefit corresponding to the prescription drug from a benefit processor based on the at least one eligibility record;
   providing the coverage benefit upon presentation of the cellular message by the cellular communication device and purchase of the prescription drug; and
   updating the at least one eligibility record to reflect the coverage benefit upon purchase of the prescription drug.

24. The method of claim 23, further comprising:
   processing the at least one eligibility record by the server computer to derive a prescription refill date related to the prescription drug upon purchase;
   sending a refill reminder by the server computer to the cellular communication device prior to the prescription refill date.

25. The method of claim 24, wherein the step of sending the refill reminder includes a next discount coupon for the prescription drug, based on the at least one eligibility record related to the cellular communication device, the coverage benefit, and the drug identifier.

26. The method of claim 23, wherein the coverage benefit is selected from the group consisting of: an insured coverage and a non-insured coverage; and further comprising:
   if an insured coverage is the coverage benefit, determining a first purchase price discount per the coverage benefit and the discount coupon, for the drug prescription; and
   if a non-insured coverage is the coverage benefit, determining a second purchase price discount per solely the discount coupon, for the drug prescription.

27. The method of claim 23, further comprising:
   adjudicating the coverage benefit with the benefit processor.

* * * * *